United States Patent
Luo et al.

(10) Patent No.: US 6,319,715 B1
(45) Date of Patent: Nov. 20, 2001

(54) METHOD OF ENHANCING THE DELIVERY OF NUCLEIC ACIDS USING SILICA NANOPARTICLES

(75) Inventors: Dan Luo; W. Mark Saltzman, both of Ithaca, NY (US); Ernest Han, N. Potomac; Nadya Belcheva, Baltimore, both of MD (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/556,074

(22) Filed: Apr. 21, 2000

(51) Int. Cl.$^7$ .................................................. C12N 15/88
(52) U.S. Cl. ................ 435/455; 435/320.1; 435/325; 435/69.1; 424/450; 424/484; 424/486
(58) Field of Search .................... 435/459, 458, 435/455, 320.1, 69.1; 424/493, 484, 486, 450; 514/44

(56) References Cited

U.S. PATENT DOCUMENTS

| | | | |
|---|---|---|---|
| 4,070,283 | * 1/1978 | Kirkland | 210/31 |
| 4,752,458 | * 6/1988 | Robinson | 423/335 |
| 5,460,831 | 10/1995 | Kossovsky et al. | 424/493 |
| 5,789,213 | 8/1998 | Hui et al. | 435/172.3 |
| 5,916,803 | 6/1999 | Sedlacek et al. | 435/320.1 |
| 5,952,232 | * 9/1999 | Rothman . | |
| 5,962,427 | 10/1999 | Goldstein et al. | 514/44 |
| 6,025,337 | 2/2000 | Truong et al. | 514/44 |
| 6,051,429 | * 4/2000 | Hawley-Nelson et al. | 435/459 |

OTHER PUBLICATIONS

Kneuer, et al. International Journal of Pharmaceutics, 2000, vol. 196, pp. 257–261.*

Eck, et al. Goodman & Gilman's The Pharmacological Basis of Therapeutics, Ninth edition, 1996. McGraw–Hill, New York, pp. 77–101.*

* cited by examiner

Primary Examiner—Dave T. Nguyen
(74) Attorney, Agent, or Firm—Hodgson Russ LLP

(57) ABSTRACT

The present invention provides a method for enhancing the delivery of nucleic acid molecules to cells by increasing the concentration of cells at the cell surface. The method comprises the step of premixing of nucleic acid:vector molecules with nanoparticles that are biocompatible, reversibly associate with the nucleic acids and have a sedimentation rate which increases the concentration of the nucleic acids at the cell surface so as to enhance delivery into the cells.

7 Claims, 5 Drawing Sheets

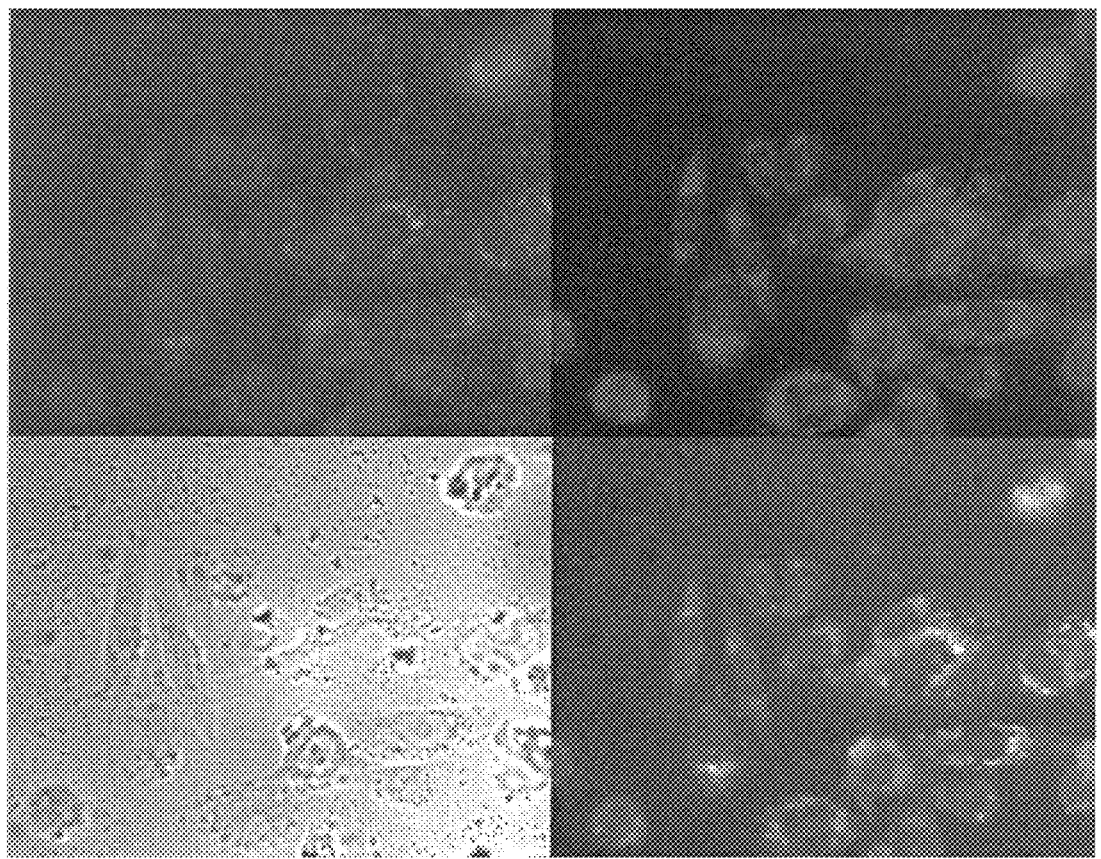

METHOD OF ENHANCING THE DELIVERY OF NUCLEIC ACIDS USING SILICA NANOPARTICLES

This invention was made with Government support from the National Sience Foundation (NSF) under Grant No. BES9986446. The Government has certain rights in the invention.

FIELD OF THE INVENTION

This invention relates generally to the area of genetic engineering. More particularly, this invention provides a method for enhancing the delivery of nucleic acids into cells using nanoparticles.

BACKGROUND OF THE INVENTION

Gene therapy and DNA vaccination are important alternatives in the treatment and prevention of inherited (e.g., cystic fibrosis), infectious (e.g., AIDS), acquired (e.g., Parkinson's disease) and neoplastic diseases. Infection by viruses, which is nature's predominant means of DNA exchange, is an efficient mechanism for gene transfer. However, clinical applications of viral mediated gene delivery have been hampered by concerns regarding safety, restricted targeting of specific cell types, limited DNA carrying capacity, recombination and high cost. Furthermore, the toxicity and immunogenicity of viral vectors also hamper their routine use in basic research settings. Therefore, non-viral gene delivery systems, especially transfection enhanced by use of chemicals have become popular in both research and clinical settings.

The efficiency of transfection of non-viral gene delivery systems is not as high as the viral-mediated systems. Consequently, a variety of chemicals have been used to increase the efficiency of nucleic acid delivery. However, these have only resulted in moderate increases in DNA delivery to cells Moreover, toxicity considerations limit the concentrations at which the chemicals can be used (Luo et al., 2000, *Nature Biotechnol.*, 18: 33–37).

U.S. Pat. No. 5,460,831 to Kossovsky et al., describes a composition of matter comprising mutilayered biodegradable core particles having a diameter less than 1 $\mu$m and having a coating (such as a carbohydrate) that binds to DNA or RNA that is to be delivered to a cell. The core particles may be further coated with targeting agents to direct DNA or RNA to desired cell types.

For transfection of cells in vitro, several parameters have to be considered. The NA uptake across a membrane is not efficient. Even if it were perfectly efficient, only a fraction of the NA molecules in the fluid could reach the cell surface over the transfection period; this fraction is substantially smaller when realistic rates of DNA uptake are considered. While the number of DNA molecules in the medium can be increased by increasing the total concentration of DNA in the fluid, transfection reagents are toxic and effective only at certain vector:NA stochiometries. Thus, it is not feasible to increase the concentration of DNA to increase the efficiency of transfection.

In view of the above, there is an ongoing need for identification and development of novel methods for enhancing the delivery of nucleic acids (NA) into cells that are simple and cost effective.

SUMMARY OF THE INVENTION

The present invention provides a method for enhancing the delivery of nucleic acids (NA) into cells in vitro. The method comprises incubating NA with nanoparticles. The nanoparticle-NA complexes are then allowed to sediment on to the cells. Delivery of the DNA or RNA into cells is accomplished by standard transfection agents or means.

Accordingly an object of the present invention is to provide a method for increasing the delivery of nucleic acids into cells by incubation of the nucleic acid molecules with nanoparticles and using the nanoparticle:NA complexes for delivery of NA to cells using standard methods of delivery.

Another object of the present invention is to provide a method for increasing the transfection efficiency by incubating the DNA:vector with nanoparticles, and allowing the nanoparticles to contact the cells in the presence of standard transfection agents or means.

BRIEF DESCRIPTION OF THE DRAWINGS

FIGS. 3A–D are representations of fluorescence microscopy of FITC-labeled DNA. FIG. 3A represents FITC labeled DNA. FIG. 3B represents differential interference contrast image of the cell morphology. FIG. 3C represents Lysotrack-Red labeled lysosomes while FIG. 3D represents its superimposed image.

DETAILED DESCRIPTION

The disclosures of all references cited herein are incorporated herein by reference.

Figure 1:
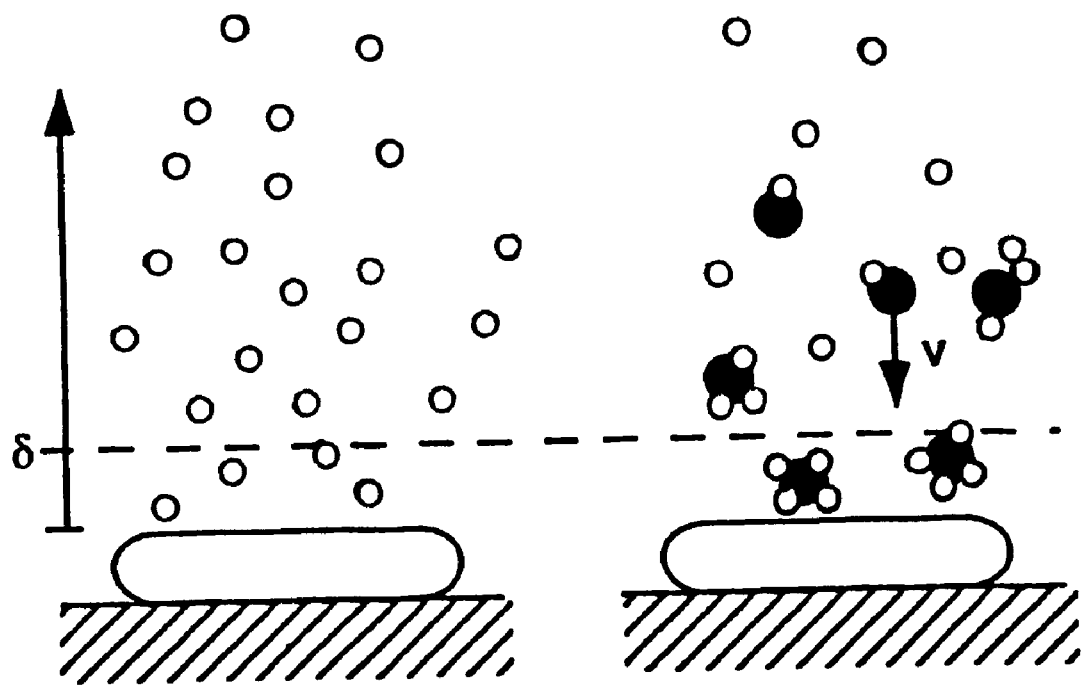
FIG. 1 is a schematic representation of the method of the present invention.

The present invention describes a method for enhancing the delivery of nucleic acids into cells by standard transfection methods. The method (illustrated in FIG. 1) comprises incubating the nucleic acid molecules with nanoparticles to form reversible complexes, and allowing the nanoparticles to sediment on to the cells prior to or during standard transfection methods. The term nanoparticles or beads as used herein refers to particles of radius between about 1 nm to about 1 $\mu$m. While not intending to be bound by any particular theory, it is believed that the method of the present invention involves, in part, increasing the local concentration of the NA in the vicinity of cells without having to increase the total concentration of the NA or the tranfecting agent in the medium.

For the present invention, the desired properties of the nanoparticles are that they have little or no toxicity i.e. they are biocompatible, that they reversibly associate with nucleic acids or nucleic acid:vector complexes; and that they sediment through aqueous solutions so as to increase the concentration of the nucleic acids at the surface of the cells. It is preferred that the beads do not aggregate (i.e., that they be mostly monodispersed).

An example of suitable nanoparticles for the present invention are silica particles. These particles are commercially available (Polysicence Laboratories). It was observed that silica particles having a sedimentation rate of at least 0.5 mm/hour were suitable for the present invention. This corresponds to silica beads of radius 50 nm having a density of 2.6 g/L. In a preferred embodiment, the radius of the beads is between about 50 nm to about 1 µm. In a more preferred embodiment, the radius of the beads is about 225 nm. Silica beads are generally available commercially in water. These can be sterilized or may be used directly. The beads may be diluted in water or in a suitable buffer before incubation with nucleic acids.

Those skilled in the art will recognize that the reactive groups on the silica beads may be modified, such as by oxidation. Those skilled in the art will also recognize that any polymer beads with similar diameter and density as the silica beads used herein can be used for the present invention. The reactive groups on the polymer beads can also be modified so as to be similar to those (such as silanol groups) on silica beads.

For the present invention, nanoparticles are incubated with the nucleic acid molecules to enable formation of reversible NA:nanoparticle complexes. While no minimum period of incubation is required, an incubation period of 5 to 10 minutes was generally used. The mixture can be used for delivery of the nucleic acids to cells using standard transfection means.

Any standard method of transfection can be used for the present invention. In general, two non-viral approaches have been used for transfection of cells. The first approach is wherein the nucleic acids are introduced by biochemical methods and the second approach is wherein the nucleic acids are introduced by physical methods. Biochemical methods include, but are not limited to, pinocytotic uptake of DNA-calcium phosphate or DNA-dextran, and liposome mediated, peptide mediated or polymer mediated transfection methods. Physical transfection methods useful in the present invention include, but are not limited to, electroporation, shockwave and particle bombardment. These methods are described in Luo et al. (2000, supra) and incorporated herein by reference.

The DEAE-dextran based transfection was first described by Vaheri et al., (1965, *Virology*, 27:424–436), which disclosure is incorporated herein by reference. For this method, DEAE dextran, which is positively charged, is exposed to the DNA and binds to the negatively charged phosphate groups of the DNA, forming aggregates Typically, target cells are rinsed, and the DEAE-dextran/DNA mixture is added to the cells. After a suitable period of incubation, (such as 10–30 minutes) cells are washed and then incubated in a suitable growth medium. The optimal concentration of DEAE-dextran and the time of incubation varies with the cell type and can easily be determined by those skilled in the art.

The calcium phosphate transfection method was first described by Graham et al., (1973, *Virology*, 52:456–467), and modified by Wigler et al., (1979, *Proc. Natl. Acad. Sci. USA*, 76:1373–1376), Chen et al., (1987, *Mol. Cell Biol.*, 7:2745–2752), and Wurm et al., (U.S. Pat. No. 5,593,875), the disclosures of which are incorporated herein by reference. This method is based on the formation of insoluble calcium phosphate-DNA precipitates. The calcium ions bind to the negatively charged phosphate groups of the DNA. The phosphate ions help to precipitate the complex. While not intending to be bound by any particular theory, it is believed that the complexes attach to the surface of a target cell and are endocytosed. In general, the method comprises incubating the cells with calcium phosphate-DNA complex for a suitable time (such as 6–12 hours), and washing the cells, followed by incubation in a suitable growth medium.

The lipid-mediated transfection method, first described by Felgner et al., (1987, *Proc. Natl. Acad. Sci. USA*, 84:7413–7416, which disclosure is herein incorporated by reference), is based on the formation of positively charged liposomes that attach to the negatively charged DNA and are attracted to the plasma membranes of target cells. For the present invention, cationic, anionic or neutral liposomes or mixtures thereof can be used.

Cationic peptides may also be used as transfection agents in the present invention. These include the cationic peptide poly-L-lysine, protamine sulfate and short peptides derived from short histone or protamine (see Luo et al., 2000 supra).

Another approach that is gaining popularity is the use of dendrimers to increase nucleic acid delivery. Polyamidoamine (PAMAM) dendrimers are a class of highly branched cationic polymers that have a well-defined architecture. These dendrimers are capable of condensing DNA and delivering it to a variety of cells lines with minimum toxicity.

Electroporation is also a common method for introducing nucleic acid sequences into cells. The method of electroporation consists of delivering high voltage pulses to target cells thereby making pores in the cell membrane to facilitate the transport of nucleic acid molecules into cells.

Other physical methods include, but are not limited to, pressure-mediated transfer (Mann et al., 1999, Proc. Natl. Acad. Sci., USA, 96:6411–6416), hydrodynamic force (Liu et al., 1999, Gene Ther., 6:1258–1266; Zhang et al., 1999, Human Gene Ther., 10:1735–1737) and ultrasonic nebulization (Pillai et al., Pharm. Res., 15:1743–1747).

The following examples illustrate the present invention and are to be construed as illustrative and not restrictive. While specific experiments are described for the delivery of DNA to cells, those skilled in the art will readily recognize that the present invention is easily applicable to the delivery of RNA or mixtures of DNA and RNA.

EXAMPLE 1

This embodiment describes the identification of materials suitable for using as nanoparticles for the present invention. The desired properties of suitable materials are 1) that the particles should sediment through an aqueous solution such as culture medium; 2) that the materials produce little or no toxicity; and 3) that the material is able to reversibly associate with the vector:nucleic acid complexes. A preferred sedimentation rate in water is at least about 0.5 mm/hr.

The sedimentation rate of particles can be determined as follows. The velocity of nanoparticle sedimentation through medium is a function of particles density $\rho_p$ and radius a:

$$v = \frac{2a^2 g(\rho_P - \rho_f)}{\mu_f}$$

where $\rho_f$ and $\mu_f$ are the density and viscosity respectively of the fluid and g is the acceleration due to gravity. By using this formula, the sedimentation rate of various materials can be calculated.

A variety of biocompatible particles were examined and their characteristics are presented in Table 1. As seen under Enhancement of gene expression, while some effect on gene expression was observed with silica particles of up to 50 nm radius, a significant effect was observed with particles of radius greater than 50 nm. Some polystyrene particles resulted in about 50% increase in enhancement of gene expression.

TABLE 1

| Material | Density (g/mL) | Radius (nm) | v (mm/hr) 37° C. | Enhancement of gene expression (%) |
|---|---|---|---|---|
| Silica | 2.65 | 225 | 8.3 (4.2)* | 750% |
|  |  | 50 | 0.4 | 42% |
|  |  | 25 | 0.1 | 10% |
| Hydroxyapatite | 3 | ~25 | 0.1 | 0 |
| Poly (lactide-co-glycolide) | 1.0 | 750 | 0.006 | 0 |
| Polystyrene | 1.05 | 44,000 | 10,000 | 50% |
|  |  | 23,000 | 3,000 | 50% |
|  |  | 500 | 1.3 | 0 |
|  |  | 30 | 0.004 | 0 |
| Polystyrene-Carboxylate | 1.05 | 225 | 0.3 | 0 |
| Polystyrene-Amino | 1.05 | 250 | 0.3 | 0 |
| Polystyrene-Hydroxylate | 1.05 | 225 | 0.3 | 0 |
| Polygold | 30 | 30 | 1.6 | 0 |

*denotes the sedimentation rate at 4° C.

EXAMPLE 2

This embodiment demonstrates that incubation of cells with nanoparticles that have been preincubated with nucleic acid complexes increases the efficiency of transfection. To illustrate this embodiment, silica nanoparticles (225 nm radius) were used. A 3.1 kb β-galactosidase DNA under the CMV promoter and BGH polyA tail was cloned into pVAX1/Lac plasmid (Invitrogen).

The CHO cells were cultured in F12K medium (ATCC) containing 10% fetal calf serum (FCS) at 37° C. in 5% CO2. Cells were plated about 24 hours prior to transfections, and were at a confluency of about 50–80% at the time of transfection. Transfections were carried out according to manufacturer's protocols (Superfect, Qiagen Inc., Valencia, Calif.; Effectene, Qiagen; Transfast, Promega, Madison, Wis.). Briefly, plasmid DNA (2 ug diluted to 100 ul of serum-free medium) was first mixed with dendrimer (10 ul of Superfect) for 5–10 min. at room temperature. The dendrimer-DNA complexes were then incubated with silica nanoparticles and incubated for another 5–10 min. Serum containing medium (600 ul containing 10% Fetal bovine serum) was then added and the mixture was then added onto the cells. The concentration of beads required for a given cell type can be empirically determined. For the CHO cells, a range of $1 \times 10^5$ beads/ul to $6 \times 10^5$ beads/ul was found to be suitable. After incubation at 37° C. and 5% $CO_2$ for 2 hours, medium containing the mixtures was gently removed, and fresh growth media were added. Cells were first lysed using an extraction reagent (Mammalian protein extraction reagent, MPER buffer, Pierce, Rockford, Ill.) and the enzyme activities were assayed using a β-galactosidase assay kit (Promega). Standard curve consisting of purified β-galactosidase protein was constructed for each experiment. The β-galactosidase activities from experimental samples were determined by comparison to the standard curve.

Figure 2A:
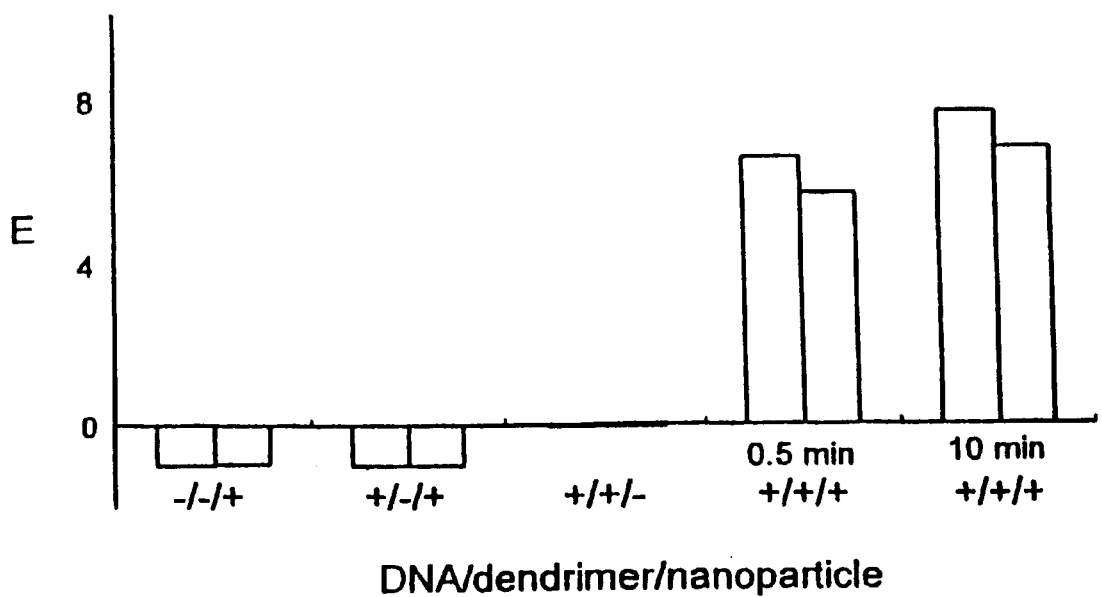
FIG. 2A is a representation of transfection in the presence or absence of DNA, transfection agent (dendrimer) or nanoparticles.
Figure 2B:
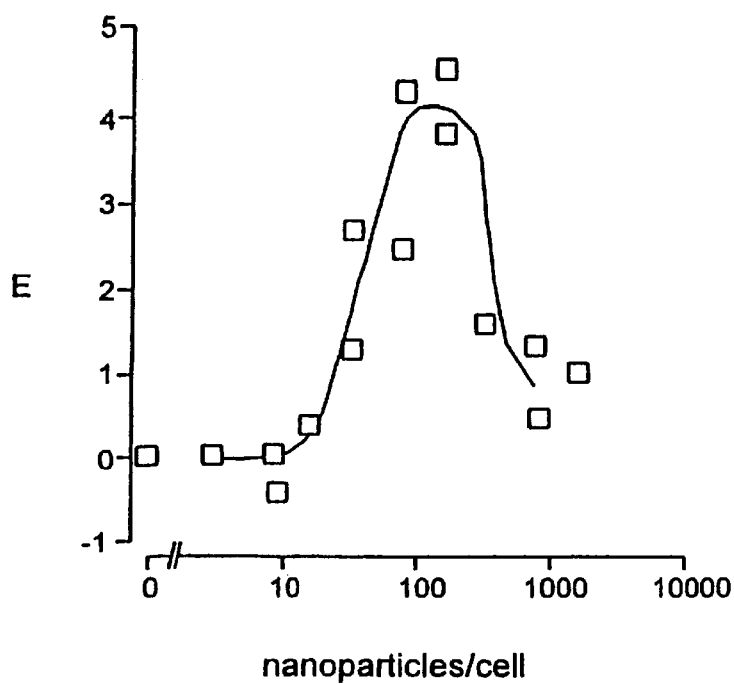
FIGS. 2B and 2C are representations of the relationship of concentration of nanoparticles and the transfection efficiency for dendrimer mediated (B) and lipid-based reagent mediated (C) transfection.
Figure 2C:
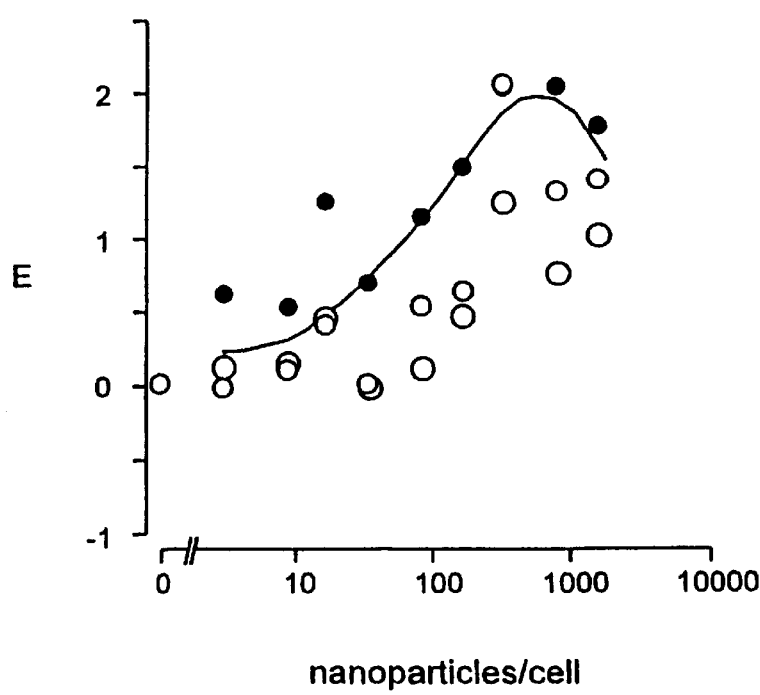

As shown in FIGS. 2A–C, brief incubation (>0.5 min.) of silica nanoparticles with vector:DNA solution before exposure to the cells produced a significant increase (up to 750%) in reporter gene expression (FIG. 2A). Nanoparticles without transfection reagent did not enhance gene expression, suggesting that the enhancement was not solely due to an increase in the rate of non-specific endocytosis or an interaction between DNA and particles. The improvement in transfection efficiency (with a fixed amount of DNA) depended on the number of particles added per cell; the greatest enhancement was observed at an intermediate ratio (about 200 particles/cell, FIG. 2A–2C). This quantity of nanoparticles had no effect on cell viability or growth: cytotoxicity was detected only at greater than 5200 particles/cell. This enhancement in expression depended on the size of the nanoparticles. Particles with an average radius of 225 nm caused enhancement (FIG. 2A–2C); particles with smaller diameter had less or no effect (Table 1).

The enhancement in the delivery of DNA described herein is not dependent upon the transfection means, since enhancement provided by the nanoparticles was observed with a variety of transfection reagents including the dendrimer-based reagent Superfect® (FIG. 2A and 2B) and the lipid-based reagents Effectene® and Transfast® (FIG. 2C), suggesting that enhancement induced by silica nanoparticles is applicable to, and consequently can be used with standard transfection methods.

The characteristics of the nanoparticle-Nucleic acid complexes were investigated by a variety of techniques, including UV-VIS spectrophotometer, fluorescence spectroscopy, and dynamic light scattering. Dendrimers used in the present invention had a characteristic absorbence at 196 nm, where the absorbance of both nanoparticles and DNA are too low to detect. DNA content was determined by a fluorodye Picogreen, which is specific to double stranded DNA. The content of silica nanoparticles was assayed by an ELISA reader at 650 nm, where the interference of dendrimers and DNA was negligible. Centrifugation at 700 rpm for 5 min. was adequate to remove nanoparticles and associated complexes from solution, leaving dendrimers, DNA, and dendrimer-DNA complexes in the supernatant; this procedure depleted DNA in the supernatant significantly, suggesting that a fraction of the DNA (<15%) was associated with the nanoparticles. No depletion of DNA was observed in the absence of dendrimer (or other transfection reagent). Laser light scattering indicated that the average diameter of particles in the 3-component solution was 20% larger than the average diameter of pure particles; a similar increase in particle size was observed by electron microscopy. When the sequence of addition of nanoparticles was altered (i.e. nanoparticles were added directly to cells first, before incubation with vector:DNA or, nanoparticles were added to cells after addition of vector:DNA), the enhancement in expression was either reduced significantly or abolished totally. While not intending to be bound by any particular theory, all of these observations are consistent with the mechanism illustrated in FIG. 1A, in which vector:DNA complexes associate reversibly with silica nanoparticles and concentrate at the cell surface.

EXAMPLE 3

This embodiment further describes the optimal conditions for enhancement of delivery of nucleic acids to cells. It was observed that continuous orbital mixing of the culture during exposure to the complexes significantly reduced the enhancement. Similarly, suspension of the cells upon a filter insert (pore size=3 μm), which was sufficiently porous to allow particles to sediment beyond the suspended cell monolayer, also abolished the enhancement effect (data not shown). Thus, it appears that local concentration of the nanoparticle:NA is required in the vicinity of cells to effect the enhancement.

Figure 4A:
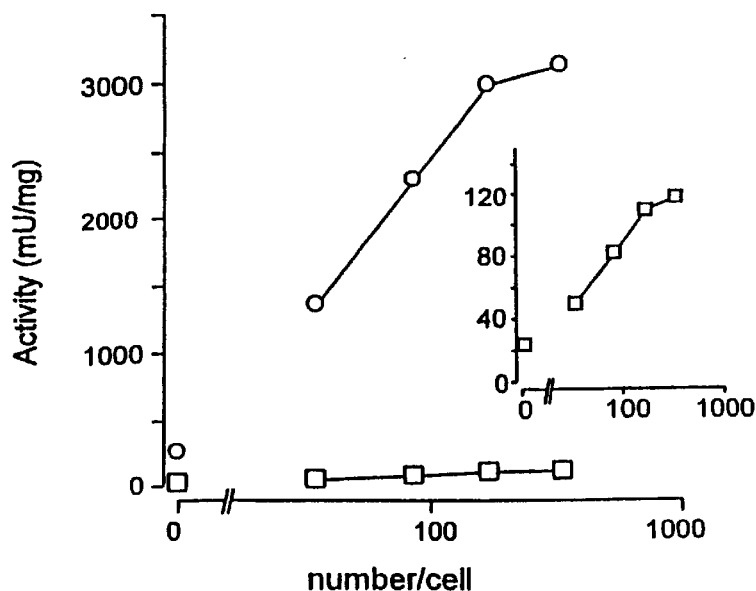
FIG. 4A and 4B are representations of the transfection efficiency at 37° C. (circles in 4A) and 4° C. (squares in 4A).
Figure 4B:
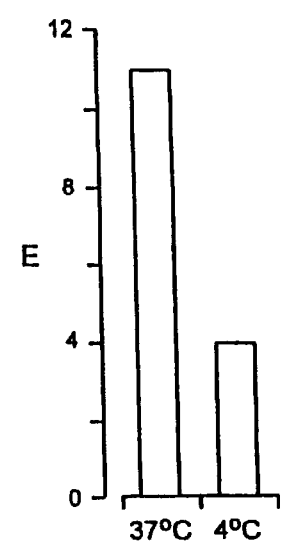

Further, to determine if the enhancement in transfection involved predominantly extracellular mechanisms quantitative fluorescence microscopy was performed. DNA was covalently labeled with FITC using a kit from PanVera (Madison, Wis.); lysosomes were stained by LysoTrack-Red (Molecular Probes, Eugene, Oreg.) according to manufacture's instructions. After transfection, cells were fixed using standard formaldehyde/glutaldehyde, and images were then captured digitally using an Olympus BX-50 fluorescence/DIC microscope with a high resolution Princeton Instruments PentaMax cooled CCD camera. Quantification were obtained by measuring the pixel intensity using a 60x oil immersion objective (n.a.=1.4) and MetaMorph imaging software (Universal Imaging Corp. West Chester, Pa.). The results shown in FIGS. 3A–3D demonstrate that the rate of endocytosis was not significantly affected by the presence of nanoparticles. To further test the endocytosis hypothesis, cells were incubated at 4° C., a well-established method for inhibiting endocytosis. Transfection efficiencies in both cases (with nanoparticles and without, FIG. 4A) were dramatically reduced (~3000%) when endocytosis was inhibited, suggesting that DNA was internalized predominantly via endocytosis under all conditions. More interestingly, when endocytosis was inhibited, the enhancement in transfection upon addition of nanoparticles was still observed (FIG. 4B).

It should be understood that while the invention has been described in detail herein, the examples provided are for illustrative purposes only. Other modifications of the embodiments of the present invention that are obvious to those of ordinary skill in the art of genetic engineering and related disciplines are intended to be within the scope of the appended claims.

We claim:

1. A method of enhancing the delivery of nucleic acids into cells in vitro comprising the steps of:
   a) forming nucleic acid-transfecting agent complexes;
   b) contacting the nucleic acid-transfecting agent complexes with silica nanoparticles to form nucleic acid-transfecting agent-nanoparticle complexes; and
   c) incubating the nucleic acid-transfecting agent-nanoparticle complexes with the cells so as to allow the nucleic acid-transfecting agent-nanoparticle complexes to sediment on to the cells during or prior to transfection,
   wherein the delivery of said nucleic acids into said cells is enhanced by said complexes, and
   wherein the transfecting agent is selected from the group consisting of lipid agent and polymer agent.

2. The method of claim 1, wherein the transfecting agent is a lipid agent.

3. The method of claim 1, wherein the transfecting agent is a polymer agent.

4. The method of claim 3, wherein the polymer agent is a dendrimer.

5. The method of claim 1, wherein the silica nanoparticles have a sedimentation rate of at least 0.5 mm/hr in an aqueous solution.

6. The method of claim 1, wherein the silica nanoparticles have a radius of between about 1 nm to about 1 $\mu$m.

7. The method of claim 6, wherein the silica nanoparticles have a radius of about 225 nm.

* * * * *